United States Patent [19]
Normann

[11] Patent Number: 4,576,182
[45] Date of Patent: Mar. 18, 1986

[54] METHOD AND APPARATUS FOR MEASURING LIQUID FLOW

[75] Inventor: Richard A. Normann, Salt Lake City, Utah

[73] Assignee: University of Utah, Salt Lake City, Utah

[21] Appl. No.: 256,689

[22] Filed: Apr. 23, 1981

[51] Int. Cl.$^4$ .............................................. A61B 5/02
[52] U.S. Cl. .................................... 128/692; 128/736; 73/204
[58] Field of Search ............... 128/691, 692, 713, 724, 128/725, 736; 73/198, 204

[56] References Cited

U.S. PATENT DOCUMENTS

| 3,438,253 | 4/1969 | Kuether et al. | 128/692 X |
|---|---|---|---|
| 3,446,073 | 5/1969 | Auphan et al. | 128/692 |
| 3,719,083 | 3/1973 | Morris et al. | 73/204 |
| 3,798,967 | 3/1974 | Gieles et al. | 128/692 |
| 4,015,593 | 4/1977 | Elings et al. | 128/713 |
| 4,236,527 | 12/1980 | Newbower et al. | 73/204 |
| 4,240,441 | 12/1980 | Khalil | 128/692 |
| 4,297,881 | 11/1981 | Sasayama et al. | 73/204 |
| 4,306,453 | 12/1981 | Wolfshorndl | 73/204 |
| 4,319,483 | 3/1982 | Durham, Jr. et al. | 73/204 |
| 4,335,605 | 6/1982 | Boyd | 73/204 |
| 4,384,578 | 5/1983 | Winkler | 73/204 X |

Primary Examiner—Kyle L. Howell
Assistant Examiner—Angela D. Sykes
Attorney, Agent, or Firm—Thorpe, North & Western

[57] ABSTRACT

Apparatus for measuring the flow of blood or other liquids through a channel includes a flexible catheter on the exterior wall of which are mounted a heating coil and spaced therefrom, a thermistor. The catheter is placed in a channel in which the liquid flow is to be measured so that the thermistor is positioned downstream of the heating coil. The apparatus also includes a capacitor which is charged to a certain level by a power supply source and then periodically discharged to the heating coil to cause the coil to produce heat. The heating coil thus heats liquid flowing thereby and any temperature change is detected by the thermistor and supplied to temperature measuring circuitry. This circuitry determines the temperature change in the liquid caused by the heating coil, integrates this temperature change and takes the reciprocal of the integrated temperature change, and produces therefrom a measure of the liquid flow.

11 Claims, 2 Drawing Figures

METHOD AND APPARATUS FOR MEASURING LIQUID FLOW

BACKGROUND OF THE INVENTION

This invention relates to a method and apparatus for measuring liquid flow through a channel, and more particularly for measuring cardiac output or blood flow.

Blood flow measurement has been used for a number of years to, among other things, assess heart-valve function, determine congenital heart defects such as holes in the walls of the heart chambers, and determine the efficiency of heart muscle. In general, measurement of blood flow is an important tool for diagnosing heart problems.

Perhaps the most common method of measuring blood flow involves employment of so-called thermodilution or thermal dilution techniques in which a known quantity of coolant liquid is injected into the blood stream and the temperature of the blood-coolant mixture is measured at a point downstream from the injection site. Knowing the temperature, mass and heat capacity of the coolant, and the temperature of the blood before injection, the mass flow rate of the blood can be determined by measuring the temperature profile of the blood-coolant mixture. The drawbacks of this method are the difficulty of accurately measuring the mass and temperature of each coolant liquid injection, the requirement of a trained doctor or nurse to make the coolant liquid injections each time a measurement is taken, and the possibility of an air bubble or bacterial contamination being injected with the coolant liquid each time a measurement is taken.

A number of methods have been proposed for overcoming the drawbacks of the above-described thermodilution technique. Included among these is the proposal for using a heating coil on a catheter to heat the blood continuously while measuring the blood temperature change by a thermistor positioned downstream from the coil. This and similar methods, however, also suffer from the problem of accurately determining and controlling the amount of electrical energy delivered to the coil to heat (or cool) the blood. It also suffers from blood temperature variations due to physiological mechanisms.

The above and other methods and apparatus for measuring blood flow are described in the following prior art patents: H. H. Khalil, U.S. Pat. No. 3,359,974, H. H. Khalil, U.S. Pat. No. 4,217,910, W. W. Webster, U.S. Pat. No. 3,726,269, A. M. Richards, U.S. Pat. No. 3,075,515, A. C. M. Gieles et al, U.S. Pat. No. 3,798,967, F. W. Kuether et at, U.S. Pat. No. 3,438,253 and A. W. Richardson, U.S. Pat. No. 3,478,588.

SUMMARY OF THE INVENTION

It is an object of the invention to provide a method and apparatus for providing a virtually continous measurement of cardiac output or liquid flow generally in a more precise and less labor intensive manner than heretofore provided.

It is also an object of the invention to provide such a method and apparatus in which an accurate quantity of energy may be delivered periodically to a heating coil to heat the blood or liquid whose flow is being determined to thereby achieve a high degree of reproducability in the results.

It is a further object of the invention to provide such a method and apparatus which is simple, inexpensive to implement, and totally self contained, requiring no personnel to inject quantities of coolant.

It is an additional object of the invention to provide such a method and apparatus in which a patient whose blood flow is being measured suffers relatively few dilatory effects as a result of the measurement.

The above and other objects and advantages of the invention are realized in a specific illustrative embodiment thereof which includes an elongate body member dimensioned for insertion into a channel which carries liquid, the volumetric flow rate of which is to be measured. Also included is a heat producing element disposed on the exterior of the elongate body and responsive to receipt of electrical energy for producing heat, and circuitry for successively delivering a predetermined amount of electrical energy to the heat producing element. Such circuitry might include a capacitor for storing a predetermined amount of electrical energy, a power supply source for supplying electrical power, and a switch element for alternately connecting the capacitor to the power supply source or to the heat producing element. A temperature detecting transducer is also disposed on the exterior of the elongate body at a position spaced "downstream" from the heat producing element. The transducer is coupled to temperature measuring circuitry for determining the profile of the temperature change in the liquid flowing past the transducer as a result of the liquid being heated by the pulse of heat produced by the heating element. The temperature profile is integrated and the reciprocal of this integrated profile is proportional to volumetric liquid flow rate. In this manner, the liquid flow rate may be determined.

The described arrangement allows for a totally self contained device as well as for precise control of the amount of energy delivered to the heating element to heat the liquid. As a result of the latter, greater accuracy can be achieved in making the liquid flow measurement.

BRIEF DESCRIPTION OF THE DRAWINGS

The above and other objects, features and advantages of the present invention will become apparent from a consideration of the following detailed description presented in connection with the accompanying drawings in which.

DETAILED DESCRIPTION

Figure 1:
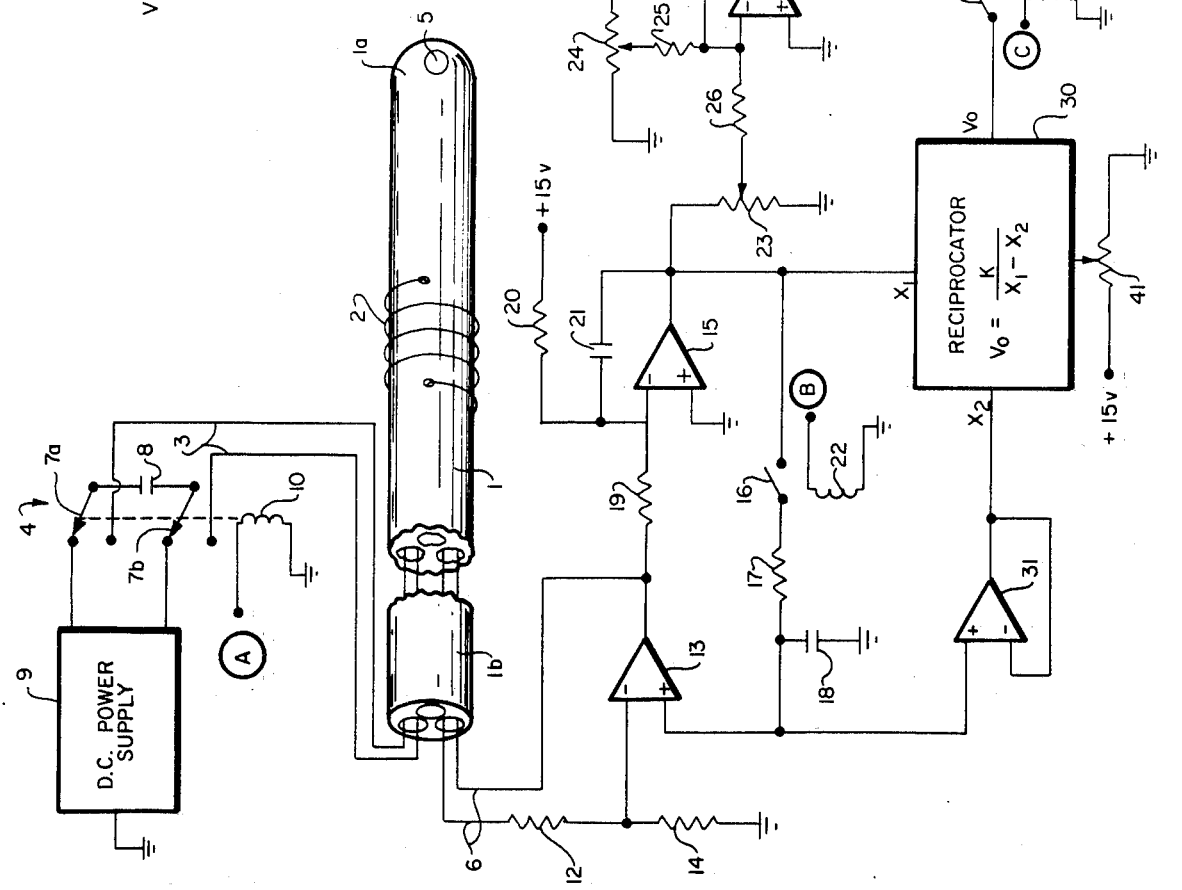
FIG. 1 is a circuit schematic showing liquid measurement apparatus made in accordance with the principles of the present invention.

Referring to FIG. 1, there is shown a circuit schematic of one specific illustrative embodiment of the present invention. Included in the embodiment is an elongate, flexible tri-lumen catheter 1. As will be discussed more fully later, liquid flow measurement is made by placing the catheter 1 in the channel carrying the liquid to be measured so that the distal end 1a of the catheter is oriented downstream of the flow of the liquid. The liquid then flows exterior to and along the length of the catheter from the proximal end 1b to the distal end 1a. The position of the catheter relative to the heart is determined by a pressure transducer connected to one of the lumens of the catheter 1. This is a well known technique.

Wound about the catheter 1 near the distal end thereof is a coil of insulated wire 2 which is connected by electrical conductors 3 (which extend through one lumen of the catheter 1) to a relay switch 4. Alternative resistive heating elements, such as conductive plastic, could also be utilized. Also mounted on the exterior of the catheter 1 and spaced "downstream" some distance from the coil 2 on the distal end of the catheter is a thermistor 5. The thermistor 5 is coupled by way of conductors 6 (which extend through another lumen of the catheter 1) to the temperature measuring circuitry to be described later. As the temperature of the liquid flowing past the thermistor varies, the resistance of the thermistor also varies (as is well known). Thus, the thermistor resistance provides a means for measuring the temperature of the liquid flowing thereby. For blood flow measurement, the spacing between the coil 2 and the thermistor 5 advantageously is about 6 inches. The dimater of the catheter 1 for use in blood flow measurement advantageously is about 3/32 inches.

Switch 4 is a conventional double-pole, double-throw switch in which two movable contacts 7a and 7b are each connected to a different side of a capacitor 8. In the unenergized state, the movable contacts 7a and 7b are connected to a power supply 9. When the relay switch 4 is energized by application of an appropriate current pulse to relay coil 10, the movable contacts 7a and 7b make contact with respective ones of the conductors 3. The current pulse applied to the relay coil 10 is supplied by a conventional clock timing circuit 11 via output lead A. Thus it can be seen that the capacitor 8 is connected either to the power supply or to the conductors 3, but not both, at any one time. This feature will help protect the subject from ground loops or other electrical hazards as well as provide a precise pulse of energy to the heating coil 2.

An alternative arrangement to the switch 4 and capacitor 8 arrangement for successively delivering precise amounts of electrical energy to the heating coil 2 would be provision of a switch which would successively connect the D.C. power supply 9 or other source of electrical energy directly to the heating coil for precise periods of time.

One of the conductors 6 from the thermistor 5 is connected to a linearizing resistor 12 which serves to make the current through the thermistor more nearly proportional to temperature. Resistor 14 is coupled between resistor 12 and ground potential. The series connection of the thermistor 5 and resistor 12 is located in a feedback loop of the input stage of an operational amplifier 13. The operational amplifier 13 is configured to function as a non-inverting amplifier whose gain is given by the ratio of the sum of resistance of resistor 12 and thermistor 5 to the resistance of resistor 14. The amplifier 13 produces a voltage output proportional to the change in resistance of the thermistor 5 and thus proportional to the change in temperature of liquid flowing past the thermistor.

The non-inverting input of operational amplifier 13 is coupled to the output of an integrating operational amplifier 15 by way of a resistor 17 and relay switch 16. The resistor 17 and a capacitor 18 (coupled between the non-inverting input of the amplifier 13 and ground) act as a low pass filter. The output of operational amplifier 13 is coupled via a resistor 19 to the inverting input of the operational amplifier 15 which is configured as a summing integrator. Coupled between the inverting input of operational amplifier 15 and a voltage source is a resistor 20. A capacitor 21 is coupled between the output and inverting input of the operational amplifier 15. The non-inverting input of amplifier 15 is grounded.

Operational amplifiers 13 and 15 act in a negative feedback mode and serve to maintain current flowing through the thermistor 5. This circuit also serves as a sample and hold circuit through the operation of the relay switch 16. Relay 16 is normally energized by the clock 11 via output lead B which is connected to coil 22 of the relay. While relay switch 16 is closed, the capacitor 18 is charged to some predetermined level. When the relay switch 16 is opened (voltage goes to zero on output lead B of the clock 11), the capacitor 18 provides a substantially constant voltage input to the non-inverting input of the operational amplifier 13 until the relay switch is again energized. In other words, the output voltage of the operational amplifier 15 is maintained at substantially the same level after the relay switch 16 is opened as it was just before opening unless blood temperature changes. This output is approximately proportional to blood temperature and, of course, would change as the blood temperature changed.

Circuitry for providing a display of the blood temperature includes a potentiometer 23 coupled between the output of the operational amplifier 15 and the inverting input of another operational amplifier 28. The non-inverting input of the operational amplifier 28 is coupled to ground. Also coupled to the inverting input of the amplifier 28 is a second potentiometer 24. A resistor couples the output of the amplifier 28 to the inverting input. This circuitry is connected in a variable gain, variable offset configuration. Potentiometer 23 reduces the gain of the operational amplifier 28 and potentiometer 24 provides a D.C. offset voltage. The output of the amplifier 28 is coupled to a digital display circuit 29, such as Allied Electronic circuit no. 667-8010, which converts the analog output to a digitally displayed number representing the blood temperature.

The apparatus of the present invention is designed to measure cardiac output and, to accomplish this, as will be discussed more later, the temperature profile of the blood, following its heating, must be integrated. This integration is carried out by the operational amplifier 15 whose output is supplied to a reciprocator circuit 30. A second input to the reciprocator 30 is supplied by another operational amplifier 31 whose non-inverting input is coupled to the capacitor 18 and to the non-inverting input of amplifier 13, and whose inverting input is coupled to the output of amplifier 31. Amplifier 31 operates as a voltage follower to sample the voltage across the capacitor 18, and serves to balance the steady output signal of operational amplifier 15. In particular, amplifier 31 supplies a voltage $X_2$ to the reciprocator 30 and this voltage is subtracted from the voltage $X_1$ supplied by the amplifier 15.

The reciprocator circuit 30 produces a voltage output representing the reciprocal of $X_1$ minus $X_2$. When relay 16 is closed, $X_1 = X_2$, so that the reciprocator circuit produces no meaningful output. When relay 16 is opened, the output $X_2$ of the amplifier 31 remains at the value it was just prior to opening the relay. The output $X_1$ of amplifier 15 now represents the integrated value of the temperature profile of the blood and the output $V_o$ of the reciprocator circuit 30 is proportional to the reciprocal of the integrated temperature profile. A potentiometer 41 is connected to the reciprocator circuit 30 to allow for adjustment of the gain of the circuit. Advantageously, the reciprocator circuit 30 is circuit no. AD534 produced by Analog Devices, Inc.

The remaining part of the circuitry of FIG. 1, other than displays and alarms, is a sample and hold circuit consisting of a relay switch 33, resistor 34, capacitor 35, operational amplifier 36 and the gain adjusting resistors 37 and 38. This sample and hold circuit samples the reciprocated temperature profile near the end of the timing sequence (FIG. 2) in response to a timing pulse C from clock 11 which causes relay 33 to close. The sampled value is maintained until the next timing cycle, and in this manner it provides an output voltage proportional to cardiac output.

The output of amplifier 36 is supplied to a digital display device 39 which provides a digital representation of the cardiac blood flow. The output is also supplied to an alarm circuit 40 which sounds an audible alarm when the output is either above a certain level or below a certain level. Advantageously, the display device 39 is the same type as that suggested for display device 29. The operation of the circuit of FIG. 1 will now be briefly described for measuring blood flow or cardiac output of a person.

To measure cardiac output of a person, the catheter 1 is inserted through the person's superior vena cava into the heart so that the thermistor 5 will be positioned in the pulmonary artery and the coil 2 will be positioned in the right atrium.

Figure 2:
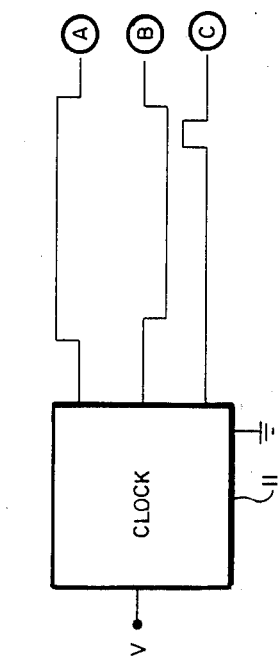
FIG. 2 is a graphic representation of the clock signals produced by the clock of FIG. 1.

When in place in the pulmonary artery and heart, the clock 11 is actuated to begin supplying clock or timing signals shown in FIG. 2 and labeled A, B and C. These labels correspond to the circuit input points of FIG. 1 where such timing signals are supplied.

When the relay switch 4 is in the unactuated state, the capacitor 8 is connected to the power supply 9 so that the capacitor is charged to its full capacity. Of course, when the capacitor 8 reaches its predetermined maximum charge, no further charging takes place. When the timing signal A shown in FIG. 2 is supplied to input A of the coil 10 of FIG. 1, the relay switch 4 is actuated to connect the capacitor 8 to the conductors 3 so that the charge on the capacitor is supplied via the conductors to the coil 2. This charge is substantially constant each time the relay switch 4 is actuated since the timing signal A is selected to occur at intervals sufficient to allow full charging of the capacitor 8 and then full discharge thereof. The coil 2 quickly produces a pulse of heat in response to the pulse of current and this heats the blood flowing past the coil 2 toward the thermistor 5 in the pulmonary artery of the patient. Operational amplifier 13 causes a constant current to flow through the thermistor 5. As the temperature of the blood and therefore the temperature of the thermistor varies, the output voltage of amplifier 13 will change to keep the current through the thermistor constant. In particular, as the temperature increases, the resistance of the thermistor 20 decreases and the output voltage of amplifier 13 decreases. When timing signal B of FIG. 2 is supplied to input B of the relay 22 to de-energize the relay, the capacitor 18 maintains its charge at the voltage level being received from the amplifier (integrator) 15 at the time the timing signal is supplied. Thus, the input to the operational amplifier 13 is at a constant level and therefore so is the output of the operational amplifier 13. Any subsequent change in the resistance of the thermistor causes the operational amplifier 13 to produce a voltage output proportional to the resistance of the thermistor, and thus proportional to the temperature change in the blood. This voltage output is supplied to the amplifier 15.

The volumetric flow rate following injection of a pulse of heat, Q (in Joules=$\frac{1}{2}$ CV$^2$), into the blood is given by $$F = Q/(p_b c_b \int \Delta T dt)$$

where $p_b$ is the density of blood in Kg/m$^3$; $c_b$ is the specific heat of blood in Joules/Kg °K., and flow rate is in units of m$^3$/sec. Q is determined by the value of capacitance 8 used and the voltage to which it is charged, and $p_b$ and $c_b$ are constants of human blood.

As is well known in blood flow measurement using thermodilution, the blood flow is proportional to the reciprocal of the integral of the temperature change produced in the blood. Thus, the output of the integrator 15 is supplied to the reciprocator circuit 30 which produces a reciprocal of the output of the integrator 15 and supplies this to the sample and hold circuitry composed of elements 32, 33, 34, 35, 36, 37 and 38. While the timing signal B (negative going) is still being supplied to the relay 16, another timing signal C, which is supplied to relay 33 terminates and then begins again (also negative going) to cause capacitor 35 to maintain a voltage output equal to the voltage output of the reciprocator 30 at the time of receipt of the beginning of the next timing pulse C. This output thus represents a measure of the blood flow and this measure is supplied to the display unit 39 for visual display.

The alarm 40 is also provided so that if the blood flow measure is above or below certain predetermined safe limits, the alarm will be set off providing an audible signal to the person attending the patient. With this arrangement, blood flow measurements may be made on a periodic basis to provide a convenient way of monitoring the blood flow of a patient. This method obviates the need of introducing a coolant liquid into the person's blood stream as required in thermodilution techniques.

After the termination of the negative going timing signal B to coil 22, relay 16 closes again so that the voltage output signal from the integrator 15 is again supplied to capacitor 18, and also to the operational amplifier 28 as earlier discussed. The output of the operational amplifier 28 is a measure of the temperature of the blood flowing past the thermistor and is supplied to the display unit 29 for display. The potentiometer 23 is provided for calibrating the display unit 29 in a well known fashion.

In the manner described, an efficient and easy to use method and apparatus for measuring volumetric blood (or liquids generally) flow is provided. Since the current pulses to heat the coil 2 can be accurately controlled and limited, very accurate blood flow measurements may be made and dilatory effects on the blood from continuous heating can be minimized. The circuit described provides not only for giving a measure of blood flow, but also for producing an audible alarm if the blood flow rate exceeds or falls below certain limits. Also, a measurement of the blood temperature is provided.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. Apparatus for measuring liquid flow through a channel comprising
   an elongate body member dimensioned for insertion into the channel,
   means disposed on the said body member for producing heat in response to receipt of electrical energy,
   means for successively delivering to said heat producing means a predetermined amount of electrical energy, said delivering means including
      means for storing a predetermined electrical charge,
      power supply means for supplying electrical current, and
      switch means for alternately connecting the storing means to the power supply means and to the heat producing means, and
   temperature measuring means disposed on the said body member and spaced downstream of said heat producing means for measuring the change in temperature of the liquid flowing thereby through the channel, said change occurring as a result of heat produced by said heat producing means.

2. Apparatus as in claim 1 wherein said temperature measuring means comprises
   transducer means disposed on the said body member and coupled to said power supply means, said transducer means varying the electrical current passing therethrough as the temperature of the liquid varies,
   integrator means coupled to said transducer means for producing a signal proportional to the integral of the change in current in said transducer means,
   reciprocator means coupled to said integrator means for producing a signal representing the reciprocal of the signal produced by the integrator means, and
   display means for producing a visual display of the signal value produced by the reciprocator means.

3. Apparatus as in claim 2 wherein said temperature measuring means further comprises alarm means for producing an audible signal when the signal value produced by the reciprocator means exceeds a first level or falls below a second level.

4. Apparatus as in claim 2 wherein said switch means is responsive to a first timing signal for connecting the storing means to the heat producing means, and wherein said temperature measuring means further comprises
   a sample and hold circuit means interconnecting said reciprocator means and said display means, said sample and hold circuit means being responsive to a second timing signal for supplying to the display means the signal produced by the reciprocator means at the time the second timing signal is supplied, and
   clock means for supplying the first timing signal to said switch means and for supplying the second timing signal to said sample and hold circuit means a predetermined period of time after supplying the first timing signal.

5. Apparatus as in claim 2 wherein said temperature measuring means further comprises second display means for producing a visual display of the signal value produced by the integrator means.

6. Apparatus as in claim 5 wherein said switch means is responsive to a first timing signal for connecting the storing means to the heat producing means, and wherein said temperature measuring means further comprises
   a first operational amplifier means having a first input coupled to the transducer means and an output coupled to the integrator means for producing a voltage output signal in response to the resistance of the transducer means
   a second sample and hold circuit means coupled between the output of the integrator means and a second input of the first operational amplifier means for connecting the integrator means and first operational amplifier means when no timing signal is present, and being responsive to a third timing signal for supplying to the first operational amplifier means while in the third timing signal is present, the signal being produced by the integrator means at the time the third timing signal is initially supplied,
   a second operational amplifier means interconnecting the integrator means to the second display means, and
   clock means for supplying the first timing signal to said switch means and for supplying the third timing signal to said second sample and hold circuit means a certain time after supplying the first timing signal.

7. Apparatus as in claim 2 wherein said transducer means comprises a thermistor.

8. Apparatus as in claim 1 wherein said body member is an elongate, flexible catheter having one or more lumens for carrying electrical conductors which connect the heat producing means and the temperature measuring means to other elements of the apparatus.

9. Apparatus as in claim 1 wherein said heat producing means comprises an insulated resistance heating element disposed on the exterior of the body member.

10. Apparatus for measuring liquid flow through a channel comprising
    an elongate body member dimensioned for insertion into the channel,
    means disposed on said body member for producing a pulse of heat,
    transducer means disposed on said body member and spaced downstream of said heat producing means for varying its resistance as the temperature of the liquid varies,
    means coupled to the transducer means for producing a voltage output signal which is proportional to the change in resistance in the transducer means,
    integrator means coupled to said voltage producing means for producing a signal proportional to the integral of the change in the output signal from said voltage producing means,
    a sample and hold circuit means coupling the output of the integrator means to an input of said voltage producing means and for passing the output signal of the integrator means to the voltage producing means when no timing signal is present, and being responsive to a timing signal for supplying to the voltage producing means while the timing signal is present the signal being produced by the integrator means at the time the timing signal is initially supplied, clock means for supplying a timing signal to said sample and hold circuit means a certain time after said pulse of heat is produced, reciprocator means coupled to said integrator means for producing a signal representing the reciprocal of the signal produced by the integrator means, and display means for producing a visual display of the signal value produced by the reciprocator means.

11. A method of measuring liquid flow in a channel comprising inserting a catheter into the channel, said catheter including a heating element and transducer spaced apart on the catheter, providing a power supply for supplying electrical current, providing a storage unit for storing a predetermined electrical charge, alternately connecting the storage unit to the power supply and to the heating element to thereby deliver to the heating element a predetermined amount of electrical energy, the heating element thereby producing a pulse of heat in response to receipt of the electrical energy, detecting the temperature change in the liquid by the temperature measuring transducer, and producing a measure of the liquid flow from the temperature change detected by the transducer.

* * * * *